(12) United States Patent
Irimescu et al.

(10) Patent No.: US 6,905,850 B2
(45) Date of Patent: Jun. 14, 2005

(54) PROCESS FOR THE PRODUCTION OF GLYCERIDES WITH LIPASES

(75) Inventors: Roxana Irimescu, Hachioji (JP); Kiyomi Furihata, Hachioji (JP); Kazuhiko Hata, Hachioji (JP); Tsuneo Yamane, Nagoya (JP)

(73) Assignee: Nippon Suisan Kaisha, Ltd., Tokyo (JP)

( * ) Notice: Subject to any disclaimer, the term of this patent is extended or adjusted under 35 U.S.C. 154(b) by 111 days.

(21) Appl. No.: 10/311,350

(22) PCT Filed: Jul. 2, 2001

(86) PCT No.: PCT/JP01/05718

§ 371 (c)(1),
(2), (4) Date: Aug. 21, 2003

(87) PCT Pub. No.: WO02/06505

PCT Pub. Date: Jan. 24, 2002

(65) Prior Publication Data

US 2004/0033571 A1 Feb. 19, 2004

(30) Foreign Application Priority Data

Jul. 13, 2000 (JP) ......................................... 2000-213359

(51) Int. Cl.$^7$ ................................................. C12P 7/64
(52) U.S. Cl. ....................................... 435/134; 554/169
(58) Field of Search ........................... 435/134; 554/169

(56) References Cited

PUBLICATIONS

R. Irimescu et al., Utilization of Reaction Medium–Dependent Regiospecificity of *Candida antarctica* Lipase (Novozym 435) for the Synthesis of 1,3–Dicapryloyl–2–docosahexaenoyl (or eicosapentaenoyl) Glycerol, JAOCS, vol. 78, No. 3, pp. 285–289 (Mar. 2001).

U. Schmid et al., Optimization of the Reaction Conditions in the Lipase–Catalyzed Synthesis of Structured Triglycerides, JAOCS, vol. 75, No. 11, pp. 1527–1531 (1998).

R. Irimescu et al., Enzymatic Synthesis of 1,3–Dicapryloyl–2–eicosapentaenoylglycerol, JAOCS, vol. 77, No. 5, pp. 501–506 (May 2000).

H. Breivik et al., Preparation of Highly Purified Concentrates of Eicosapentaenoic Acid and Docosahexanoic Acid, JAOCS, vol. 74, No. 11, pp. 1425–1429 (1997).

*Primary Examiner*—Deborah D. Carr
(74) *Attorney, Agent, or Firm*—Westerman, Hattori, Daniels & Adrian, LLP

(57) ABSTRACT

The invention provides a process for producing 2-monoglycerides (2-MG) or triglycerides (TG), particularly triglycerides having polyunsaturated fatty acid (PUFA) residues in the sn-2 positions, at an extremely high purity and a high efficiency.

The 2-MG is produced by conducting alcoholysis of a starting TG with a first 1,3-lipase. Then, the TG is produced by introducing fatty acid residues to the 1- and 3-positions of the produced 2-MG by using a second 1,3-lipase. The fatty acid residue in the 2-posiiton is preferably a residue of DHA, EPA or ARA. The "first lipase" refers to one which is selective for the 1- and 3-positions and can act even on a long-chain fatty acid in alcoholysis, while the "second lipase" refers to one which is selective for the 1- and 3-positions and can produce a TG through the reaction of a 2-MG with a fatty acid ester or a free fatty acid.

8 Claims, No Drawings

PROCESS FOR THE PRODUCTION OF GLYCERIDES WITH LIPASES

TECHNICAL FIELD

The present invention relates to a process for manufacturing glycerides with lipases. More particularly, the present invention relates to a process for producing 2-monoglycerides or triglycerides, in particular triglycerides (TG) having polyunsaturated fatty acid (PUFA) residues in the sn-2 positions, by using lipases.

In the present invention, "DHA" is an abbreviation representing docosahexaenoic acid, "EPA" is an abbreviation representing eicosapentaenoic acid, and "ARA" is an abbreviation representing arachidonic acid. When expressions "DHA enriched fat" and "tri-DHA-triglyceride" are employed, "DHA" is employed as an abbreviation representing a docosahexaenoic acid residue.

Also, "MG" represents a monoglyceride, "2-MG" represents a 2-monoglyceride, and "TG" represents a triglyceride.

Further, "first lipase" refers to one which is selective for the 1- and 3-positions and can act even on a long-chain fatty acid in alcoholysis.

"Second lipase" refers to one which is selective for the 1- and 3-positions and can produce a TG through the reaction of a 2-MG with a fatty acid ester or a free fatty acid.

BACKGROUND ART

When introducing any desired fatty acids to the 1- and 3-positions using a lipase that is selective for the 1- and 3-positions, it is general to employ a method of conducting acidolysis with an objective fatty acid, or a method of conducting ester interchange of an objective fatty acid ester. With those methods, however, a much excessive amount of fatty acid or ester must be used. Also, from the viewpoint of probability theory, a part of original fatty acids in the 1- and 3-positions remain. It is therefore relatively difficult to obtain a lipid having the objective structure at a high purity.

Further, because lipases have the activity greatly changeable depending on the chain lengths of fatty acids and the activity upon long-chain fatty acids, such as DHA, are extremely weak, a lipid having the objective structure cannot be obtained in some cases.

Lipases cause reactions such as hydrolysis, interesterification, acidolysis, and esterification. However, there are lipases having various characteristics, and all kinds of lipases do not develop the same degree of reactivity under the same conditions in all of the reactions. For example, the use of a 1,3-lipase having a strong reactivity for acidolysis is advantageous in substitution of fatty acids in the 1- and 3-positions, but when that lipase does not have a sufficient reactivity for DHA, etc., a much difficulty arises in substitution of a TG having DHA in the 1- and 3-positions for another objective fatty acid. Of course, the objective substitution can be achieved by using a lipase having a high activity not only for acidolysis, but also for DHA. Such a lipase is, however, difficult to obtain or is very expensive. Hence industrial use of that lipase is disadvantageous.

DISCLOSURE OF THE INVENTION

An object of the present invention is to provide a process for producing a 2-MG or a TG, particularly a TG having polyunsaturated fatty acid (PUFA) residues in the sn-2 positions, at an extremely high purity and a high efficiency.

The present invention resides in a process for producing glycerides, wherein a 2-MG is produced by conducting alcoholysis of a starting TG with a first 1,3-lipase.

A fatty acid residue in the 2-position is a residue of DHA, EPA or ARA. In this case, the present invention resides in a process for producing glycerides, wherein an MG with a fatty acid residue in the 2-position being a residue of DHA, EPA or ARA is produced by conducting alcoholysis of a starting TG with a first 1,3-lipase.

The starting TG is a fat containing a polyunsaturated fatty acid, preferably a DHA enriched fat, an EPA enriched fat or an ARA enriched fat. In this case, the present invention resides in a process for producing glycerides, wherein a 2-MG is produced by conducting alcoholysis of a fat containing a polyunsaturated fatty acid, preferably a DHA enriched fat, an EPA enriched fat or an ARA enriched fat, with a first 1,3-lipase.

The fat is fish oil. In this case, the present invention resides in a process for producing glycerides, wherein a 2-MG is produced by conducting alcoholysis of fish oil, preferably DHA enriched fish oil or EPA enriched fish oil, with a first 1,3-lipase.

The starting TG is a tri-DHA-TG, a tri-EPA-TG or a tri-ARA-TG. In this case, the present invention resides in a process for producing glycerides, wherein a 2-MG is produced by conducting alcoholysis of a tri-DHA-TG, a tri-EPA-TG or a tri-ARA-TG with a first 1,3-lipase.

Also, the present invention resides in a process for producing glycerides, wherein an objective TG is produced by introducing a fatty acid residue to each of the 1- and 3-positions with a second 1,3-lipase via the above-mentioned 2-MG, i.e., a 2-MG produced by conducting alcoholysis of a starting TG with a first 1,3-lipase.

A fatty acid residue in the 2-position is a residue of DHA, EPA or ARA. In this case, the present invention resides in a process for producing glycerides, wherein an objective TG is produced by introducing a fatty acid residue to each of the 1- and 3-positions with a second 1,3-lipase via an MG with a fatty acid residue in the 2-position being a residue of DHA, EPA or ARA, which is produced by conducting alcoholysis of a starting TG with a first 1,3-lipase.

The fatty acid residue introduced to each of the 1- and 3-positions is a medium-chain saturated fatty acid residue having the carbon number of 8, 10 or 12. In this case, the present invention resides in a process for producing glycerides, wherein an objective TG is produced by introducing a medium-chain saturated fatty acid residue having the carbon number of 8, 10 or 12 to each of the 1- and 3-positions with a second 1,3-lipase via a 2-MG, preferably an MG with a fatty acid residue in the 2-position being a residue of DHA, EPA or ARA, which is produced by conducting alcoholysis of a starting TG with a first 1,3-lipase.

The starting TG is a fat containing a polyunsaturated fatty acid, preferably a DHA enriched fat, an EPA enriched fat or an ARA enriched fat. In this case, the present invention resides in a process for producing glycerides, wherein an objective TG is produced by introducing a fatty acid residue to each of the 1- and 3-positions with a second 1,2-lipase via a 2-MG which is produced by conducting alcoholysis of a fat containing a polyunsaturated fatty acid, preferably a DHA enriched fat, an EPA enriched fat or an ARA enriched fat with a first 1,3-lipase.

The fat is fish oil. In this case, the present invention resides in a process for producing glycerides, wherein an objective TG is produced by introducing a fatty acid residue to each of the 1- and 3-positions with a second 1,2-lipase via a 2-MG which is produced by conducting alcoholysis of fish oil, preferably DHA enriched fish oil or EPA enriched fish oil, with a first 1,3-lipase.

The starting TG is a tri-DHA-TG, a tri-EPA-TG or a tri-ARA-TG. In this case, the present invention resides in a process for producing glycerides, wherein an objective TG is produced by introducing a fatty acid residue to each of the 1- and 3-positions with a second 1,2-lipase via a 2-MG which is produced by conducting alcoholysis of a tri-DHA-TG, a tri-EPA-TG or a tri-ARA-TG with a first 1,3-lipase.

A preferred mode of the process for producing glycerides according to the present invention is featured in that an objective TG is produced by introducing fatty acid residues to the 1- and 3-positions with a second 1,2-lipase via a 2-MG which is produced by conducting alcoholysis of a starting TG with a first 1,3-lipase. In other words, the present invention provides a method utilizing two stages of reactions of lipases, i.e., comprising the steps of preparing a 2-MG through alcoholysis of a TG with a first 1,3-lipase, and preparing a TG through esterification of the 2-MG with a second 1,3-lilpase by using lower alkyl esters of fatty acids or free fatty acids to be introduced to the 1- and 3-positions.

The inventors have discovered that, even when some kind of lipase cannot provide a satisfactory result in acidolysis and hydrolysis through the reaction with TG, it is possible to essentially completely remove fatty acids in the 1- and 3-positions and to obtain 2-MG by conducting alcoholysis of the TG with such a lipase in spite of fatty acids such as DHA, for which the lipase has a low reactivity, being present in the 1- and 3-positions. Also, the inventors have discovered that TG having the objective structure can be produced at an extremely high purity and a high efficiency by acting, upon the 2-MG, fatty acid esters or free fatty acids which are to be introduced to the 1- and 3-positions thereof. The present invention has been accomplished by combining those procedures in a proper sequence.

The first lipase used in the first stage is not limited to particular one so long as it is selective for the 1- and 3-positions and is able to act even on a long-chain fatty acid, such as DHA, when subjected to alcoholysis, such as ethanolysis and methanolysis. A preferable example of lipases usable for that purpose is *Candida antarctica* lipase (e.g., Novozym 435 [made by Novo Nordisk Bio Industry Co., Ltd.].

The second lipase used in the second stage is not limited to particular one so long as it is selective for the 1- and 3-positions and is able to produce TG through reaction of 2-MG and fatty acid esters or free fatty acids under reduced pressure. A preferable example of lipases usable for that purpose is *Rhizomucor miehei* lipase (e.g., Lipozymel M [made by Novo Nordisk Bio Industry Co., Ltd.]. The fatty acid esters include, for example, lower alkyl esters such as ethyl ester.

In an optimum mode of the manufacturing method according to the present invention, a TG having the objective structure is produced by introducing fatty acid residues to the 1- and 3-positions with Lipozymel M via a 2-MG produced by conducting alcoholysis of a starting TG with Novozym 435.

The starting TG is preferably a fat containing a polyunsaturated fatty acid, and the polyunsaturated fatty acid is DHA, EPA or ARA. The starting TG used in the method of the present invention is, e.g., fish oil, preferably a DHA enriched fat, a tri-DHA-TG, an EPA enriched fat, a tri-EPA-TG, an ARA enriched fat, or a tri-ARA-TG. The fatty acid used in the method of the present invention to be introduced to each of the 1- and 3-positions is preferably a saturated fatty acid having the carbon number of 8, 10 or 12.

When a tri-DHA-TG made up of highly-purified DHA only is used as the starting TG in the present invention, a TG of X-DHA-X type can be obtained at a high purity. It is quite difficult to obtain such a TG with conventional combinations of acidolysis and commercially available lipases. Further, by selecting medium-chain fatty acids having the carbon numbers of 8 to 12 as the fatty acids introduced to the 1- and 3-positions in the above case, a DHA-containing TG with a superior absorptivity can be obtained, and it is expected to have a great effect when employed in powdered milk or the like for infants.

Also, a lipid having the structure containing EPA can also be prepared in a similar way. By obtaining an EPA-containing TG with a superior absorptivity, foods, medicines and so on having various physiological activities specific to EPA are expected.

Further, it is known that fish oil contains DHA localized in the 2-position. By applying the present invention to tuna oil or bonito oil which has a relatively high DHA content, a fat having an increased absorptivity and a superior nutritive value can be obtained. In addition, by employing, as starting fish oil, fish oil having a DHA concentration enriched by wintering or any other suitable method, TG having the objective structure and containing DHA in even higher amount can be obtained.

By dividing the reaction of lipases into two stages and conducting alcoholysis of TG with the first 1,3-lipase in the first stage, even from DHA or the like having, in the 1- and 3-positions, fatty acids for which lipases have low reactivity, it is possible to essentially completely remove the fatty acids in the 1- and 3-positions and to obtain 2-MG.

Then, by conducting esterification of the 2-MG with the second 1,3-lipase in the second stage by using lower alkyl esters of fatty acids or free fatty acids which are to be introduced to the 1- and 3-positions, TG having the objective structure can be produced at an extremely high purity and a high efficiency.

BEST MODE FOR CARRYING OUT THE INVENTION

Details of the present invention will be described in conjunction with Examples. It is to be noted that the present invention is limited in no way by Examples set forth below.

EXAMPLE 1

The mixture of 1 g of bonito oil, 3 g of ethanol, and 0.4 g of Novozym 435 were agitated at 35° C. for 2 hours in a flow of nitrogen gas. After the reaction, a lipid composition of the reaction mixture was measured by the Iatroscan method. As a result, 69.5% of ethyl ester, 2.3% of diglycerides, and 28.3% of MG were detected, but TG and free fatty acids were not detected. As a result of analysis using thin layer chromatography, it was confirmed that MG was 2-MG. Further, as a result of measuring a fatty acid composition by gas chromatography, DHA in the starting bonito oil was 27.9%, while DHA in the obtained MG was 51.5%.

EXAMPLE 2

The mixture of 1 G of oil, which was prepared through wintering of starting sardine oil with acetone used as a solvent for enrichment of PUFA, 3 g of ethanol, and 0.4 g of Novozym 435 were agitated at 35° C. for 3 hours in a flow of nitrogen gas. After the reaction, a lipid composition of the reaction mixture was measured by the Iatroscan method. As a result, 67.7% of ethyl ester, 1.9% of diglycerides, and 30.4% of MG were detected, but TG and free fatty acids were not detected. As a result of analysis using thin layer chromatography, it was confirmed that MG was 2-MG. Further, as a result of measuring a fatty acid composition by gas chromatography, DHA in the oil prepared through wintering was 13.0%, while DHA in the obtained MG was 28.8%.

EXAMPLE 3

The mixture of 0.184 g of glycerin, 0.184 g of water, and 0.239 g of Novozym 435 were agitated for 30 minutes. After adding 1.971 g of DHA, the mixture was agitated all the night at 60° C. under reduced pressure of 3–5 mmHG. After filtering the enzymes, the reaction mixture was refined using a silica gel column. As a result, 1.83 g of tri-DHA-TG (purity of 99% and yield of 89%) was obtained.

The mixture of 0.102 g of thus-obtained tri-DHA-TG, 0.306 g of ethanol, and 0.046 g of Novozym 435 were agitated at 35° C. for 4 hours in a flow of nitrogen gas. After filtering the enzymes, a composition of the glyceride fraction was analyzed by the latroscan method. As a result, 92.7% of MG, 5.35% of diglycerides, and 1.96% of TG were detected. As a result of analysis using thin layer chromatography, it was confirmed that 100% of MG was 2-MG.

EXAMPLE 4

To all of the reaction mixture, 0.345 g of ethyl octanoate, 0.010 g of water, and 0.050 g of Lipozyme IM were added, which was prepared in a similar way as that in Example 3 and from which ethanol remaining after filtering the enzymes was removed through fractionation under reduced pressure. The mixture was agitated at 35° C. for 30 minutes in a flow of nitrogen gas. Then, the pressure in the reaction container was reduced to 3–5 mmHg by a vacuum pump while the agitation was continued at 35° C. for 3.5 hours. A composition of the glyceride fraction of the thus-obtained reaction mixture was analyzed by gas chromatography and high-speed liquid chromatography with a silver ion column. As a result, 81.4% of TG having DHA in the 2-position and octanoic acids in the 1- and 3-positions was contained.

EXAMPLE 5

0.289 G of octanoic acids, 0.010 g of water, and 0.050 g of Lipozyme IM were added to 0.040 g of 2-DHA-MG, which was obtained through fractionation of the reaction mixture prepared in a similar way as that in Example 3. The mixture was agitated at 35° C. for 30 minutes in a flow of nitrogen gas. Then, the pressure in the reaction container was reduced to 3–5 mmHg by a vacuum pump while the agitation was continued at 35° C. for 3.5 hours. A composition of the glyceride fraction of the thus-obtained reaction mixture was analyzed by gas chromatography and high-speed liquid chromatography with a silver ion column. As a result, 78.8% of TG having DHA in the 2-position and the octanoic acids in the 1- and 3-positions was contained.

EXAMPLE 6

The mixture of 0.184 g of glycerin, 0.184 g of water, and 0.239 g of Novozym 435 were agitated for 30 minutes. After adding 1.815 g of EPA, the mixture was agitated all the night at 60° C. under reduced pressure of 3–5 mmHG. After filtering the enzymes, the reaction mixture was refined using a silica gel column. As a result, 1.74 g of tri-EPA-TG (purity of 99% and yield of 92%) was obtained.

The mixture of 0.094 g of thus-obtained tri-EPA-TG, 0.283 g of ethanol, and 0.038 g of Novozym 435 were agitated at 35° C. for 4 hours. After filtering the enzymes, a lipid composition of the glyceride fraction was analyzed by the latroscan method. As a result, 98.5% of MG, 5.35% of diglycerides, and 0.42% of TG were detected. As a result of analysis using thin layer chromatography, it was confirmed that 100% of MG was 2-MG.

EXAMPLE 7

To all of the reaction mixture, 0.400 g of ethyl decanoate, 0.010 g of water, and 0.050 g of Lipozyme IM were added, which was prepared in a similar way as that in Example 6 and from which ethanol remaining after filtering the enzymes was removed through fractionation under reduced pressure. The mixture was agitated at 35° C. for 30 minutes in a flow of nitrogen gas. Then, the pressure in the reaction container was reduced to 3–5 mmHg by a vacuum pump while the agitation was continued at 35° C. for 3.5 hours. A composition of the glyceride fraction obtained after the reaction was analyzed by gas chromatography and high-speed liquid chromatography with a silver ion column. As a result, 72.7% of TG having EPA in the 2-position and decanoic acids in the 1- and 3-positions was contained.

EXAMPLE 8

0.345 G of decanoic acids, 0.010 g of water, and 0.050 g of Lipozyme IM were added to 0.037 g of 2-EPA-MG, which was obtained through fractionation of the reaction mixture prepared in a similar way as that in Example 6. The mixture was agitated at 35° C. for 30 minutes in a flow of nitrogen gas. Then, the pressure in the reaction container was reduced to 3–5 mmHg by a vacuum pump while the agitation was continued at 35° C. for 3.5 hours. A composition of the glyceride fraction obtained after the reaction was analyzed by gas chromatography and high-speed liquid chromatography with a silver ion column. As a result, 70.6% of TG having DHA in the 2-position and the decanoic acids in the 1- and 3-positions was contained.

INDUSTRIAL APPLICABILITY

According to the present invention, a process for producing TG is obtained which can produce TG having the objective structure, in particular TG having PUFA in the sn-2 position at an extremely high purity and a high efficiency.

Also, the present invention provides a process for producing 2-MG that is particularly useful as an intermediate product for producing TG having the objective structure.

What is claimed is:

1. A process for producing glycerides, wherein a 2-monoglyceride is produced by conducting alcoholysis of a starting triglyceride with a first 1,3-lipase.

2. A process for producing glycerides, wherein, by introducing a fatty acid residues to each of the 1- and 3-positions with a second 1,3-lipase via a 2-monoglyceride produced by conducting alcoholysis of a starting triglyceride with a first 1,3-lipase, triglycerides each being of a structure having, in the 2-position, a fatty acid residue derived from the starting triglyceride and, in the 1- and 3-positions, the same fatty acid residue newly introduced are obtained.

3. A process for producing glycerides according to claim 2, wherein the fatty acid residue in the 2-position is a residue of DHA, EPA or ARA.

4. A process for producing glycerides according to claim 2 or 3, wherein the fatty acid residue introduced to each of the 1- and 3-positions is a medium-chain saturated fatty acid residue having the carbon number of 8, 10 or 12.

5. A process for producing glycerides according to any one of claims 1 to 4, wherein the starting triglyceride is a fat containing a polyunsaturated fatty acid.

6. A process for producing glycerides according to claim 5, wherein the fat is a DHA enriched fat, an EPA enriched fat or an ARA enriched fat.

7. A process for producing glycerides according to claim 5 or 6, wherein the fat is fish oil.

8. A process for producing glycerides according to claim 1 or 2, wherein the starting triglyceride is a tri-DHA-triglyceride, a tri-EPA-triglyceride or a tri-ARA-triglyceride.

* * * * *